United States Patent [19]

Key

[11] Patent Number: 4,975,377
[45] Date of Patent: Dec. 4, 1990

[54] CELL GROWTH CHAMBERS AND METHOD OF USE THEREOF

[76] Inventor: Marc E. Key, 20 Washington St., Novato, Calif. 94947

[21] Appl. No.: 50,510

[22] Filed: May 14, 1987

[51] Int. Cl.[5] .................. C12M 3/00; C12M 3/04; B01L 3/00
[52] U.S. Cl. .................................. 435/284; 435/285; 435/286; 435/287; 435/297; 435/299; 435/300; 435/301; 435/240.25; 435/240.243; 422/102
[58] Field of Search ............ 422/102; 206/1; 428/35; 435/284, 285, 286, 287, 297, 299, 300, 301, 240.25, 240.243

[56] References Cited

U.S. PATENT DOCUMENTS

| | | | |
|---|---|---|---|
| 3,997,396 | 12/1976 | Delente | 195/1.8 |
| 4,024,020 | 5/1977 | Weiss et al. | 195/1.8 |
| 4,224,413 | 9/1980 | Burbidge | 435/284 |
| 4,352,887 | 10/1982 | Reid et al. | 435/240 |
| 4,440,860 | 4/1984 | Klagsbrun | 435/240 |
| 4,442,206 | 4/1984 | Michaels et al. | 435/68 |
| 4,495,282 | 1/1985 | Ohnishi et al. | 435/68 |
| 4,559,304 | 12/1985 | Kasai et al. | 435/240 |
| 4,661,460 | 4/1987 | Sakuma | 436/165 |

FOREIGN PATENT DOCUMENTS 61-74579 9/1984 Japan.
0821484 4/1981 U.S.S.R..

OTHER PUBLICATIONS

Folkman and Moscona, "Role of Cell Shape in Growth Control", vol. 273 (1 Jun. 1978), pp. 345–349.

Primary Examiner—Esther L. Kepplinger
Assistant Examiner—Toni R. Scheiner
Attorney, Agent, or Firm—Burns, Doane, Swecker & Mathis

[57] ABSTRACT

Growth chambers for anchorage-independent cell growth therein are formed of a gel matrix having a surface disallowing anchorage-dependent cell growth over the full interior thereof. In a preferred form the chambers have a generally cylidnrical wall and an integral convex bottom wall forming an annular volume at the foot of the cylindrical wall which is substantially lower than the central portion to concentrate such anchorage-indpendent cells. The gel matrix is sufficiently permeable to permit passage of cell-growth nutrients and waste product solutes through said wall when the chambers are filled below the open end and submerged in a growth medium. Preferably the gel matrix is formed of 1% to 5% cross-linked polyacrylamide and from 99% to 95% water.

In a preferred method of using the growth chambers, undifferentiated tumor cells and normal cells, including fibroblasts, are cultured together. Anchorage-independent tumor cells proliferate while anchorage-dependent cells are unable to grow without attachment. The method is useful for evaluating in vitro therapeutic agents to control tumor growth, normal cell growth or microspheres and generation of immunoglobulins from lymphocyte cells.

5 Claims, 1 Drawing Sheet

CELL GROWTH CHAMBERS AND METHOD OF USE THEREOF

FIELD OF THE INVENTION

The present invention relates to cell-growth chambers for in vitro cell culture either to grow anchorage-independent cells, which do not require a solid substratum for growth, or to grow anchorage-dependent cells, which require a solid substratum for growth as monolayers. More particularly, the invention relates to a method for carrying out in vitro assay of anchorage-independent tumor cells in the presence of anchorage-dependent normal cells and without interference by competing growth of such normal cells, including fibroblasts.

It is a particular object of the invention to grow selectively explanted tumor cells while suppressing anchorage-dependent (normal) cell growth to permit prompt measurement of the effectiveness of therapeutic agents on the rate of growth of such tumor cells. In carrying out the method, explanted tumor cells are grown on a semi-solid matrix without separation from normal cells, including fibroblast cells. Such growth does not require isolation of tumor stem cells or embedding tumor cells in a semi-solid or solid permeable growth matrix. Further, growth chambers of this invention passively incubate desired cells without mechanical intervention, as by pumping or stirring to replenish nutrients or remove waste or growth products. Thus the potential of mechanical damage of cells during their growth period is avoided.

In accordance with the invention, cell-growth chambers are formed of a gel matrix having a surface over the full interior of the chamber which prevents or rejects attachment of cells that require attachment surfaces in order to proliferate or grow in number. The chamber is also particularly characterized by high permeability of the walls, generally formed with an inner cylindrical surface and an integral convex bottom so that most of the cells are confined to an annular cell-growth volume around the foot of the cylindrical surface. This volume is substantially lower than the central portion of the bottom, so that anchorage-independent tumor cells (which require no attachment surface for qrowth), after suspension in a growth feeder or nutrient medium concentrate or congregate by gravity in the annular volume. Accordingly, cell-to-cell contact or proximity of other cells tends to accelerate growth of such anchorage independent cells. In the preferred method of growing cells, the growth chamber walls are substantially immersed in a growth media by filling the chamber to a depth slightly below the open edge of the cylindrical wall and with the chamber supported in a larger volume support chamber, such as a petri dish. The nutrient medium level in the support chamber is then adjusted so that both the inner and outer cylindrical walls of the growth chamber are substantially submerged but without liquid communication over the open upper end.

Because the growth chamber is formed of a highly permeable gel matrix, as described below, the growth feeder medium and metabolic waste products or growth solutes from the growing cells pass through the chamber walls by molecular and ion diffusion. Thus, waste products diffuse outwardly through the cylindrical wall. At the same time, growth media components, such as protein, polypeptides, amino acids, sugars, salts, etc., readily diffuse into the growth chamber. Desirably, the gel matrix passes all molecular weight components of less than one million, (also referred to as 1M daltons). Thus both growth and waste components freely diffuse through the gel matrix to transfer continuously cell-growth nutrients to growing cells and simultaneously minimize the accumulation of toxic cell metabolites produced by the growing cells. Additionally substantial submersion of the permeable gel walls maintains structural and dimensional integrity of the growth chambers.

The arrangement makes possible growth of attachment-independent cells, such as tumor cells, without interference by anchorage-dependent cells, since the highly permeable gel matrix does not provide suitable attachment surfaces. In this way comparative bioassays of the effectiveness of different therapeutic agents, or different concentrations of the same agent on the rate of tumor cell growth is possible in a few days by inexpensive spectrophotometry or colorimetric detection of the total number of live cells after incubation for a known time period.

BACKGROUND OF THE INVENTION

It has been proposed heretofore to bioassay the sensitivity of tumor cells removed surgically from humans or animals by exposing cultures of such cells to varying dosages of therapeutic agents such as drugs, or radiation by x-rays, gamma rays and the like. Such assay permits prescription of effective, but non-lethal, doses of therapeutic agents for the specific destruction of particular tumor cells, as represented by specimen cells removed from a tumor bearing host. In general, such procedures have been difficult and expensive to perform because of simultaneous growth of more prolific normal cells, including fibroblasts, with the tumor cells where attachment surfaces are available. In general, fibroblasts readily grow in vitro, frequently as the predominate cell type in a mixture of normal and tumor cells to be assayed.

Several procedures are known for isolating particular portions of tumor cells from normal cells. One particular procedure is disclosed in U.S. Pat. No. 4,411,990 issued Oct. 25, 1983 to Salmon, et al. It discloses a technique for an in vitro bioassay of human tumors by growing tumor stem-cells from explanted tumors in animals and humans, or other tumor cell lines. Tumor stem cell colonies are then propagated by plating or gelling them in a carrier nutrient medium in a permeable agar overlayer. The layer of tumor stem-cell colonies overlies a similar permeable layer containing a gelled feeder nutrient medium. The two gelled layers of the system are semi-solid, or solid, with the underlying layer serving to maintain separation of the cells from each other and from the surface of the culture dish, while providing the tumor stem-cells with the requisite feeder nutrients and growth factors. In general, the number of tumor stem-cells is within a given range, and after incubation or growth during a prescribed period of time under conventional incubation temperatures and humidity, the number of viable colony forming tumor stem-cells is counted. The cells are subjected to chemical or radiation therapy at desired doses as a measure of the specificity of such therapy for destruction of the explanted tumor stem-cells during incubation.

While the foregoing method has found application to numerous varieties of tumors, the method presents particular problems. First, it requires the careful preparation of a single cell suspension, carefully preparing both the nutrient solution and plating solution, dispersing the tumor stem cell colonies in the solidified gel and then identifying tumor stem cell colonies in the explanted cell population. The number of viable tumor stem cell colonies are counted at the end of the test and numerically analyzed. Additionally, the method is quite specific to the subjective enumeration of tumor stem cell colonies rather than tumor cells generally. Because tumor cell preparations from surgically removed tumor tissue are contaminated by normal cells including fibroblasts, and because most growth conditions are less than optimal for the tumor cells, prior known methods for growth of tumor cells within a semisolid matrix have been both erratic and unsatisfactory. Accordingly, the ability to provide a very favorable growth environment for the tumor cells to the exclusion of normal cells is made possible by practice of the present invention. Using highly permeable semisolid growth chambers having an enclosed annular volume with continuous feeding and dilution of waste products substantially simplifies such suspension culture.

It has also been known heretofore to cultivate cells and cell lines in vitro, as in glass or plastic flasks or test tubes. Such procedures are particularly suited for growth of attachment-dependent cells, including fibroblasts, which must attach to a solid substratum in order to proliferate. However in general, such growth from surgically removed tumor tissue includes attachment of both anchorage-dependent and anchorage-independent cells to the surface of the flask or test tube and results in a culture containing both normal and tumor cells.

Various methods of supporting cell growth in nutrient media have been disclosed in the prior art. Further, various surfaces have been provided which favor growth of certain cells by favoring specific growth characteristics, such as anchorage dependence.

Using prior known techniques, it has been difficult to establish various kinds of cell lines which are based on human tumor cells. In general, the success rate in establishing such growth from explanted cells of some human tumors, for example, may be as low as from 1 to 10 percent. Further, it has long been desirable to establish homogenous cell lines of indefinite life as sources of desirable biological products generated by their growth for manufacture of vaccines, antibodies, hormones, etc. Heretofore, interference by normal cells has made specific growth of some tumor cells, or clones of other cells having indefinite life, particularly difficult.

Methods of establishing current cell lines heretofore have not been satisfactory since the life span of normal cells tends to be relatively short in that they are finite; that is, the number of replications before they die appears to be genetically preset. Presently, tumor cell lines are known that are at least thirty years old, but evidence no biological change or deterioration of the growth characteristics of the cell line. Accordingly, cancer or tumor cells appear to replicate indefinitely. This permits such cells, including hybridomas or monoclonal antibodies formed therefrom (based on cell hybridization technology), to be used for long-term production of biologically useful molecules. It also makes possible measurement of the immune response of cells infected by viruses. Also, where antigens activate such cells, they may be used to develop antibodies capable of inactivating molecules such as allergens in foods or air, as well as tumors and viruses.

DISCUSSION OF THE PRIOR ART

U.S. Pat. No. 4,415,668 to Siegel is directed to growing mammalian cells on amphipathic microcarriers which contain both hydrophobic and polar groups for anchorage-dependent cells. While not discussed in detail, the patent recognizes that large scale growth of anchorage-independent cells have been grown in suspension cultures. That is, by submergence of microbial cells. There is no disclosure of growing both anchorage-dependent and anchorage-independent cells in the same suspension or any specific procedure directed to suspension and growth of anchorage-independent cells.

U.S. Pat. No. 4,565,784 to Franzblau et al is directed to use of hydrogels to support cell growth. While recognizing that anchorage-dependent mammalian cells have been grown in suspension cultures, in dishes, flasks, roller tubes, or bottles which include special attachment growth surfaces, such as collagen or other protein macromolecules. Specifically, the patent recognizes that hydrogels have desirable properties in that they are usually highly permeable to water ions and small molecules and can be made both non-toxic and compatible with tissue, but are unsuitable for cell attachment and growth. It also recognizes that hydrogels based on polyhydroxyethyl methacrylate (referred to as poly-HEMA) have been used as a coating on standard tissue culture flasks to prevent fibroblast growth. However, the patent is directed to incorporating into such materials, macromolecules, particularly protein collagen, to support cell growth. The adhesion of cells to the substrate is said to be advantageous in that the entire substrate may be removed from the culture dish to transfer cells. The amount of macromolecule added to the surface is said to control mechanical stresses on cells. Cross-linking of the polymeric structure for three-dimensional stability of the gel in aqueous solution uses dicrylate dimethacrolates or other divalent molecules. Additional cross linking may be with UV radiation. The patent states that small molecules are not used in the hydrogel since only macromolecules provide a suitable substrate for attachment growth of cells. Alternatively, polysaccharides are suggested as one of the macromolecules. The patent indicates that fibroblast cells do not grow on HEMA hydrogels containing no collagen and that collagen is either added, or the cells themselves are induced to produce collagen by adding ascorbic acid or by otherwise contacting them with collagen. The patent contains no disclosure of specific chamber structure for suspension growth for tumor cells or methods of using such chambers to grow tumor cells in the presence of fibroblast cells.

U.S. Pat. No. 4,440,860 to Klagsbrun discloses a method of promoting cell growth of malignant cancerous or transformed cells in the absence of fibronectin or transferrin by the use of colostrum and milk. Such growth is without proliferation of fibroblasts or embryo cells resulting in overgrowth of fibroblasts so that proliferation of the desired cells is promoted. Use of defatted colostrum and milk in the nutrient medium does not kill or stimulate proliferation of eukaryotic cells so that the rate of cell proliferation is proportional to the concentration of malignant cells in the sample.

U.S. Pat. No. 4,559,304 to Kasai et al discloses the use of a culture dish for in vitro growth of animal cells on a collagen substrate chemically modified with amino or carboxylic groups to improve attachment and proliferation of fibroblasts or macrophages in the presence or absence of bovine fetus serum.

U.S. Pat. No. 4,024,020 to Weiss et al discloses the use of polyacrylonitrol surfaces on hollow fibers for monolayer cell growth of mammalian cells by attachment to the polyacrylonitrol surface. The patent indicates that cells inherently incapable of proliferation, such as erythrocytes, cannot be cultured on such surfaces. This technique is also described in U.S. Pat. No. 3,997,396 to Delente. The patent particularly discloses that normal or unaltered mammalian cells, possessing a normal number of chromosomes for the species, regenerate only a relatively predictable number of times before senescence or death. The patent also discloses that unless the oxygen supply is properly provided in adequate quantities to normal cells, the cells will not maintain their normal differentiated functional state and that it is difficult to attain tissue-like densities on the growing surface because of problems pertaining to nutrient diffusion within the tissues. The hollow fiber is made permeable to gas but impermeable to cells. Materials suitable for such tubes are polyolefins such as polyacrylonitrol and polystyrene.

U.S. Pat. No. 4,352,887 to Reid et al is directed to in vitro culture of epithelial cells. The method is directed to use of connective-tissue-derived fibers as a substrate for differentiated cell culture. The patent particularly points out the difficulties of culturing individual cell types outside of an organ or a tissue culture.

U.S. Pat. No. 4,495,282 to Ohnishi et al is directed to in vivo or in vitro cell culture by implanting a human cell line in a non-human warm-blooded animal or by supplying nutrient body fluid from such an animal to a conventional type diffusion chamber. No particular structure for the diffusion chamber is disclosed.

U.S. Pat. No. 4,224,413 to Burbidge discloses apparatus for culturing cells in a vessel having a porous matrix which permits adherence of cells to the vessel. The patent particularly discloses disadvantages of submerged or suspension culture techniques. They include maintaining complex nutrient media characteristic and concentration used to cover the cell. Good growth conditions are obtained in a mechanically rotated bottle so that the cells are covered only by a thin film of growth media. It proposes to feed a monolayer of cells attached to a solid porous medium by a foam which breaks upon contact with the matrix. The foam produces a thin film throughout the matrix and over cell surfaces and leaves gas in the interstitial spaces. The method is particularly directed to culture of human fibroblasts.

U.S. Pat. No. 4,442,206 to Michaels et al discloses apparatus for growing microbial cells in isotropic hollow fibers. Nutrient media passes over and into the fibers to nourish the cells. Product is recovered from the tubes or with the effluent of the nutrient media flowing over the tubes.

Japanese application No. 86140074/22, Kokai No. 61-74579, is directed to the use of conical vessels in which attachment-dependent cells are adhered by centrifugal force. PCT application Ser. No. WO-83/02954 is directed to the use of solid polystyrene particles coated with ionically bonded proteins for anchorage-dependent cell culture. Polystyrene and divinylbenzene are cross linked as copolymers to form microcarriers or beads for suspension culture of normal cells which grow only if they become attached to an appropriate surface. The patent is particularly directed to growth of mammalian cells on microcarriers beads formed of DEAE-Sephadex, a species of dextran. Alternate materials are polyacrylamides. Certain materials are indicated to be unsatisfactory for attached cell growth due to their swelling in aqueous solutions, particularly where pore size is sufficiently large to allow wasteful entry of essential nutrient regulators. Polystyrene divinylbenzene beads are used to limit the pore size to about 350 daltons.

Folkman and Moscona disclose in "Nature" Vol. 273, 1 June 1978, the use of poly-HEMA (two hydroxyethyl methacrylate) as a culture dish coating to control the growth of anchorage-dependent cells. The coating prevents overcrowding and avoids developing cells having a spherical or hexagonal configuration. The report indicates that adhesive forces modulate cell shape to permit or prevent DNA synthesis. It also suggests that continual proliferation of malignant C cells is due to the ability of such cells to proliferate in solution growth because tumor cells surmount diffusion problems of crowding. It is suggested that growth is due to tumor cells overcoming close cell packing to continue DNA synthesis, whereas attachment-dependent cells are dependent upon lateral space to continue such DNA synthesis. No structure is disclosed for concentrating tumor cells or for continuously passively feeding and removing wastes from cells during suspension culture.

SUMMARY OF THE INVENTION

In accordance with the present invention, the foregoing difficulties of growing tumor cells, without requiring segregation of tumor-stem cells and without agitation or mechanical manipulation, is made possible by a cell-growth chamber capable of growing anchorage-independent tumor cells without interference by normal cells, including fibroblasts. The growth chamber is constructed of a gel matrix having a high percentage of liquid so that the surface suppresses or inhibits attachment of anchorage-dependent cells to the matrix surface over the full chamber interior. The chamber is characterized in that it retains its desired shape when autoclaved and while substantially immersed in a cell-growth medium. The matrix structure additionally has a high permeability for diffusion of molecular components having a molecular weight of less than one million daltons, so that complex, selected nutrients and biological products freely diffuse through the wall. This permits passive transfer of cell-growth nutrients and dilution of metabolic waste solutes during incubation. The growth chamber is particularly characterized by being formed with a substantially cylindrical sidewall and an integral convex bottom. The convex bottom forms an annular volume around the foot of the cylindrical wall which is substantially lower than the central portion. This configuration concentrates anchorage-independent tumor cells by gravity toward the annular area when suspended in the chamber growth medium. It thus assures close association of the attachment-independent tumor cells. Close association of tumor cells is know to accelerate and enhance their reproduction due to close proximity or cell-to-cell touching. Tumor cells grown in the annular volume are without interference by simultaneous growth of attachment-dependent cells in the culture medium, so that the total live cells after a given time is proportional only to the tumor cell population at the beginning of each assay even though attachment-dependent cells are present in the chamber.

In a preferred method of operation, the growth chambers are substantially submerged in a support plate, preferably a petri dish, containing sufficient growth media to maintain a level just below the upper edge of the growth chambers, which is similarly filled. Thus, the hydraulic head of the liquid (although slight) assists in diffusion of the growth medium components through the walls of the growth chamber to feed cells continuously and passively and similarly aids in diffusion of the metabolic waste products generated by the growing cells outwardly into the surrounding support media through the permeable walls of the chamber.

In another preferred method of operation using growth chambers of the present invention, an in vitro method of assaying growth sensitivity of such anchorage-independent tumor cells to varying amounts of therapeutic agents may be measured during incubation in a culture media with anchorage-dependent normal cells being present in the tumor cell preparation. In this way the ability of an agent to suppress tumor cells growth may be evaluated with varying amounts of intervention by chemotherapy agents or radiation. The method is characterized by introducing a known quantity of a single cell suspension of live tumor cells and normal cells, including fibroblasts, prepared from a surgically removed tumor specimen, into each of a plurality of chambers, and then passively incubating the cells in the growth chambers at approximately 37° C. in a $CO_2$ incubator for a period of five to seven days. The several growth chambers are disposed in a common, or single, support volume, such as a petri dish, with the same levels of growth media in each growth chamber and the support dish to feed and eliminate waste from cells growing in the individual chambers. Cells in each individual chamber are subjected to known quantities of therapeutic agent, which may be supplied either initially or periodically throughout cell growth. The number of live cells at the end of such incubation period, either sustained in their existence or multiplied in the growth chamber, is then measured without interference by anchorage-dependent cells, since the latter cells are unable to multiply or divide without anchorage in such growth chamber. Preferably, the live cell population is indirectly determined by measuring the action of a constitutive cellular enzyme on a chromogenic substrate. The color produced from such a reaction is then measured colorimetrically or spectrophotometrically.

In another important aspect of the present invention, attachment-dependent cells may be grown in growth chambers constructed in accordance with the present invention, with or without the concave bottom in the chambers, by introducing a given quantity of small solid particles, such as microspheres, having an appropriate anchorage surface for attachment of anchorage-dependent cells. Such anchorage-dependent cells, being unable to grow on the non-attachment surface of the chamber, reproduce as a monolayer on the microspheres alone. Thus, cell growth of such an anchorage-dependent line is exclusively on the spheres and may be readily harvested by removal of the spheres from the chamber.

The method is also applicable to the growth of human B-lymphocytes and the production of human immunoglobulin and/or monoclonal antibody from human B-lymphocytes grown in a serum-free media within the subject growth chambers. Since such cells are not interfered with by the growth of normal cells, which may inadvertently enter the serum-free medium either by accident or by contamination, such B-lymphocyte cultures may be incubated over a given period of time. The supernatant content of human immunoglobulin and/or human monoclonal antibody produced in the growth chambers is determined periodically, both from the medium within the growth area of the growth chamber and, in more dilute form, from the supernatant bath medium of the surrounding support container.

In another important aspect of the present invention, B-lymphocyte cells are seeded into the growth chambers of the present invention immersed in a nutrient growth medium bath. Such cells are incubated to their maximum density in the chambers and such maximum density is then maintained for long-term production of secretory products. Only the nutrient growth medium of the bath is periodically changed without diluting, removing or subculturing the B-lymphocyte cells in the chambers. Thus, the lymphocyte cells remain viable under these conditions and continue to produce secretory products which are extractable from the nutrient bath over extended periods of time.

Further objects and advantages of the present invention will become apparent from the following detailed description of the preferred article of manufacture, apparatus and method aspects of the invention, described below in connection with the accompanying drawing which form a part of the present specification.

DESCRIPTION OF THE PREFERRED EMBODIMENTS OF THE INVENTION

Figure 1:
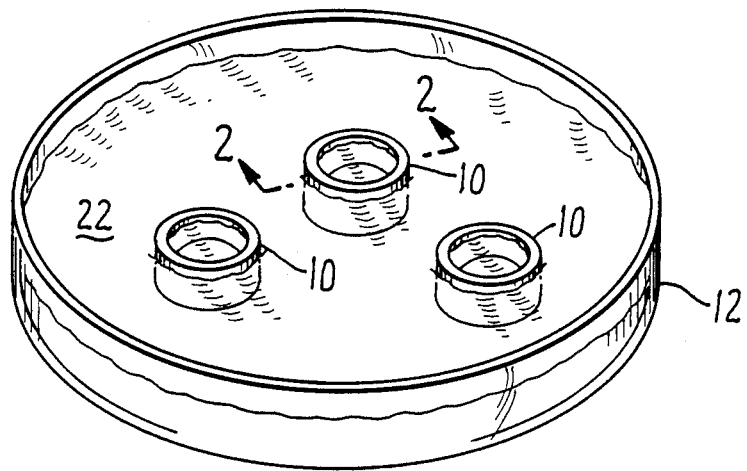
FIG. 1 illustrates in perspective an assemblage of three growth chambers constructed in accordance with the present invention and disposed in a surrounding petri dish which forms a media reservoir and support container to supply continuously, without mechanical stirring or agitation, fresh nutrient solution for growth of cells in the individual chambers and to dilute and diffuse waste products of such cell growth to the surrounding dish.
Figure 2:
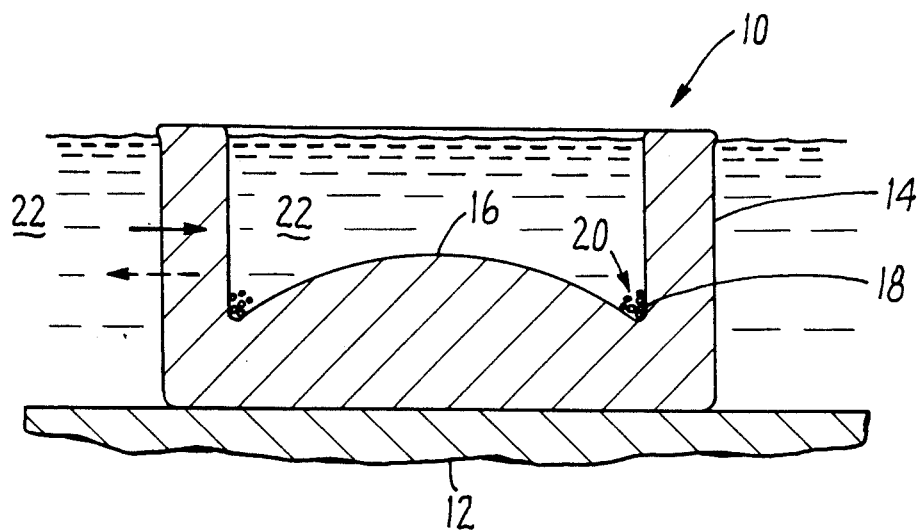
FIG. 2 is a cross-sectional view in the direction of arrows 2—2 in FIG. 1 showing a preferred configuration of the growth chambers and the preferred method of concentrating attachment-independent cells in the annular volume around the base of the cylindrical wall by submersion of cell in the growth media in the chambers and surrounding the permeable walls in media to the same depth in the support chamber.

Referring now to the drawing and in particular to FIG. 1, there is shown a preferred growth environment for tumor cells in growth chambers 10 in accordance with the method of the present invention. A plurality of growth chambers 10 are positioned within a support chamber, such as petri dish 12. FIG. 2 shows the preferred structural details of chambers 10 which include a generally cylindrical wall 14 and an integral, generally convex bottom 16 that is substantially higher at its center than at foot 18 of wall 14. This arrangement effectively forms a cell collecting annulus 20 which tends to accumulate most individual tumor (or other) cells by gravity when suspended in culture medium 22 within chamber 10. While other configurations of the growth chambers may be used, the particular merit of the annular area is that where the total volume of the growth medium in chamber 10 is on the order of 400 microliters and the total tumor cell population for the initial inoculum is relatively low, in the range of 2.0 to $7.0 \times 10^5$ viable cells, concentration of the cells for close spacing or touching is essential for rapid growth. Under such conditions, anchorage-independent cells which grow without adherence to the surface of the chamber are provided a favorable growth environment with close cell-cell association or contact. Accordingly, the shape of the bottom of chamber 10 encourages most cells to gravitate to an annular area at foot 18 of wall 14.

In the arrangement shown in FIG. 1, as noted above, three growth chambers, such as three 400 microliter chambers, may be placed in a single petri dish 12 having a 60 mm diameter and surrounded with about 5.0 ml of nutrient liquid. The growth chambers may have internal working volumes ranging from say 200 microliters to 6000 microliters for simultaneous growth of tumor cells. A series of these 60 mm petri dishes can be set up simultaneously, but each petri dish may be subject to differing amount of treatment. By filling both support dish 12 and chamber 10 to a level just below the upper edge of wall 14, cells in each growth chamber are subjected to a slight, but adequate, hydrostatic head to induce diffusion of nutrient components in the surrounding medium into the growth chamber, and diffusion of metabolic waste products outwardly through growth chamber wall 14 to dish 12.

To achieve such diffusions into and out of growth chambers 10, the material of construction for the growth chambers is preferably a gel matrix formed by cross-linking acrylamide to include a high volume of water. Such polyacrylamide gel is preferably formed by cross-linking acrylamide with bisacrylamide, and cast in the form of chambers 10, as shown. Desirably, the total solids content of such growth chambers for adequate permeability to diffuse molecules having a molecular weight of less than one million daltons is from about 0.5% to 15%, with water comprising 99.5% to 85%. Most preferably from about 0.5% to 5% and water 99.5% to 95%. The polyacrylamide so cast is highly permeable for diffusion of proteins, polypeptides, amino acids, sugars and salts in the liquid nutrient to the growing cell and for transport of cell-generated metabolic products, e.g., acids, alcohols, and other metabolic products out of chamber 12 through wall 14. Most importantly, the cross-linked acrylamide forming the gel matrix has sufficient mechanical strength to maintain the structural integrity of chambers 10 when subjected to heat and pressure, as when autoclaved to sterilize growth chambers 10. Limitation of the molecular weight of the compounds that will pass through wall 14 prevents transfer of cells or large proteins therethrough, but does not prevent passage of essential proteins or complex organic compounds in the nutrient media to the incubating cells.

Other gel materials may be used in addition to the acrylamide, such as montmorillonite or bentonite clays, agar and other gels which are essentially thixotropic and which can be cast in the desired shape of growth chambers 10 and then cured or set sufficiently to withstand mechanical handling in a saline solution during packaging, transport or handling or in a liquid feeder medium during cell culturing.

A primary requirement of the gel matrix for practice of the method of the present invention is that the material, such as the preferred cross-linked acrylamide, must be resistant to cell attachment so that anchorage-dependent cells, such as fibroblasts, do not adhere to any of the interior surfaces of the chamber. This assures that anchorage-independent cells, such as tumor cells, will grow or proliferate in the chamber, but without interference by an increasing number of anchorage-dependent cells, including fibroblasts. Thus, even though fibroblasts are present in explanted tissue along with tumor cells introduced into the growth chamber, they do not reproduce or proliferate in the chambers, unless specific growth surfaces are added to the chamber.

The attachment-independent cell surface thus restricts growth in number and type of cells to those desired in the fluid medium. Accordingly, the attachment-free surface of the growth chambers may be selectively used for (1) tumor-cell growth in the presence of (and without interference by) normal, attachment-dependent cells, (2) attachment-independent growth of lymphocyte cells, (3) attachment-dependent growth of normal cells, including fibroblasts, on particles introduced into the chamber so that all growth occurs as a monolayer on particles, such as microspheres, and (4) production of cell metabolites from either attachment-dependent, or independent cell growth, as in (1) (2) and (3), and including human monoclonal antibodies from human B-lymphocyte cultures. In production of monoclonal antibodies, attachment-independent growth is particularly useful in that B-lymphocyte cells generate large molecular weight substances, including immunoglobulins, as secretory products in the medium. Because of the passive flow of nutrient and waste products through the highly permeable walls, desired products, such as immunoglobulins, may be harvested from supernatant of the medium, both in the growth chamber and in the surrounding feeder container, without interfering with continued growth of cells or, in the case of attachment-dependent cells, the particle surface.

PREFERRED EMBODIMENT OF GROWTH CHAMBER CASTING

Cross-linked acrylamide gels are known for use in electrophoresis to identify cell protein sequences by chromatography. However, migration of cell proteins through such material is by application of an electrical field across the gel with the proteins in an SDS (sodium dodecyl sulfate) solution. In accordance with the present invention, I have found that the desired properties of growth chambers for passive, rapid culturing of tumor cells, as above set forth, may be produced by controlling the amount and degree of cross-linking of such polyacrylamide gels used to cast growth chambers 10 in accordance with the following procedure.

Three working solutions are prepared to form the casting gel.

Solution A is prepared by dissolving TRIS (a buffering compound, triamabase) in distilled water. The pH of the solution is adjusted with hydrogen chloride, and diluted to a given volume with distilled water. A minor amount of TEMED (N, N, $N^1$, $N^1$-tetra methyl ethylene diamine) is then added and the resulting solution again diluted to a final volume with distilled water.

Solution B is then prepared by mixing approximately 95% powdered acrylamide with 5% powdered methylene bisacrylamide (observing the neurotoxin hazard of such powders, until dissolved in distilled water.) The mixture is dissolved in distilled water to approximately three times the weight of the mixture of acrylamides.

Solution C is a 1.2 mg/ml solution of ammonium persulfate in distilled water.

The three solutions are then mixed in a ratio of 5:3:6 of the respective solutions A, B and C. The resultant gel mixture is then poured into growth chamber molds having the desired shape, as shown in FIG. 2. A seal is placed over each mold to insure anaerobic conditions for gelling. Preferably, the molds include sufficient riser space to assure the exclusion of air bubbles. After setting at ambient temperature, the growth chambers removed from the molds and washed extensively with distilled water and then placed in bottles containing a saline solution. The storage bottles including growth chambers are then autoclaved at 120° C. and 15 psi for approximately 20 minutes. After cooling, the chambers are then stored (in saline solution) at room temperature until used in accordance with the present invention for cell culture.

EXAMPLES OF PREFERRED METHODS OF CELL CULTURE

Following are examples that are illustrative of various methods of practicing the methods of the present invention made possible by use of growth chambers constructed in accordance with the present invention:

ONCOSCREENING METHOD

An explanted tumor specimen is processed, as by chopping, mincing and/or enzymatic digestion and the like to a single cell suspension. Three growth chambers 10 are filled and submerged in growth nutrient in a plate or petri dish 12. The desired concentration of therapeutic drug is added to the nutrient medium surrounding each growth chamber. Approximately $1.0 \times 10^5$ viable tumor cells in a total volume of 200 microliters are then pipetted from the single cell suspension into each growth chamber. The nutrient level is adjusted to just below the upper end of wall 14 and the culture is incubated for 5–7 days at 37° C. in a $CO_2$ incubator. After the desired incubation time, the plates are removed from the incubator and the nutrient medium in the petri dishes is removed and discarded. Approximately 200 microliters of cell detection substrate is pipetted into each growth chamber. The growth chambers are then incubated an additional two hours at 37° C. The resulting reaction product within each growth chamber is diluted 1:1 (vol/vol) with stop buffer. 100 microliters samples from the diluted mixture are pipetted into a 96 well microliter plate. The optical density of each well on the microliter plate is then read by color photometric means and the value related to viable cell concentration in each growth chamber.

MICROCARRIER BEAD CULTURE

Because the growth chambers are specifically designed to prevent adherence of cells to their internal surface, monolayer growth of cells is inhibited. Accordingly, most normal cells require a solid substratum to grow and will readily adhere to any solid particles with such a surface that are present. For this reason cells co-cultivated with microcarrier beads in growth chambers of the present invention readily attach to such beads. The superiority of the present chambers for microcarrier bead system over other tissue culture microcarrier bead systems derives from the fact that the cells are induced to preferentially attach to the beads, since no other solid surfaces are available for binding. Nearly all normal cells present in the culture will attach to the beads in as little as 20 to 60 minutes. Microcarrier bead cultures have a number of applications, including:
1. General tissue culture system for routine propagation and passaging of cells. Cells can be cultured at higher densities and in lower volumes because microcarrier beads provide a greater surface area per volume of growth medium than do plastic flasks.

Passaging of cells is simplified. Confluent beads from a growing culture may be pipetted, mixed with fresh beads, and then the new mixture used to reseed additional chambers. In this way, cells are passaged without using enzymes (i.e. trypsin). Thus, cells harvested in this manner can be diluted and reseeded into fresh growth chambers without an enzyme treatment to detach the cells from the surface of the growth chamber. Cells that attach and grow on the microcarrier beads are then easily processed into a single cell suspension by using collagenase rather than trypsin. This avoids the damaging affects that trypsin can have on cell membranes. Trypsin is known to alter antigenic determinants expressed on the plasma membranes of some cells.

2. Isolation of cellular secretory products.

Yields are improved because cells are grown at higher concentrations than under standard tissue culture conditions. Supernatants in the growth chambers and surrounding bath are easily removed and cells refed by simple pipetting without disturbing cell cultures, with or without microcarrier beads.

3. Preparation of confluent bead monolayers for specialized testing such as contraction of endothelial cells in response to vascular permeability factors, or in morphological studies of cell-cell interactions.

CHARACTERISTICS OF MICROCARRIER BEAD CULTURES

Upon initiation of a microcarrier bead culture, there is a rapid (within minutes) binding of cells to the surface of the bead. In the present system, binding is usually complete within 20 minutes to 2 hours. Within 24 hours the cells have spread out over the surface of the bead to form a uniform monolayer. When the beads are fully confluent, cells can be passaged by mixing together old and new beads. In general the cells prefer to remain on the original bead until no more surface area is available and then to transfer to a fresh bead.

METHOD 1 (2 hour method) is as follows:
1. Use only siliconized glassware since beads will bind to untreated glass and plastic.
2. Prepare microcarrier beads (Cytodex-3; Pharmacia) at a concentration of 6 mg/ml. Sterilize by autoclaving, and equilibrate with growth medium.
3. In a 60 mm support plate place 3 growth chambers. To the interior compartment of the growth chamber add 100 ul of microcarrier beads.
4. Add $1 \times 10^6$ cells in a 100 ul volume on top of the beads. Incubate in a 37° C., humidified, $CO_2$ incubator for 1 hour; mix culture, and incubate for 1 additional hour.
5. Beads should be maximally saturated. Excess unbound cells can be removed by the following wash procedure.

With a siliconized Pasteur pipet, pipet up contents of microcarrier bead cultures. Allow beads to sediment into the pipet tip and transfer the sedimented beads to a siliconized glass tube. Discard upper supernatant containing unbound cells. Resuspend beads in fresh medium. Repeat wash step 2 more times.
6. Loaded beads are then transferred to new growth chambers and incubated overnight to promote cell spreading.
7. Place 3 growth chamber in a 60 mm support plate. Add 200 ul of loaded beads and growth medium to inner chamber of growth chamber and 5.0 ml of growth medium to outer chamber of support plate. Place in a 37° C., humidified $CO_2$ incubator.

Method 2 (24–48 hour method) is as follows:
1. Place 3 growth chambers in a 60 mm support plate and add 5.0 ml of growth medium to the support plate.
2. Proceed as in steps 1 through 3 of Method 1.
3. On top of the beads overlay $2 \times 10^5$ cells in a 100 ul volume.
4. Place in a 37° C., humidified, $CO_2$ incubator and allow 24 to 48 hours for a confluent monolayer to form. Check with an inverted microscope.
5. Since nearly all of the cells will bind, the wash step used to remove unbound cells in Method 1 is usually unnecessary.

Growing cells in microcarrier culture.
1. Place 3 growth chambers in a 60 mm support plate and add 5.0 ml of growth medium to the plate.
2. Load microcarrier beads with cells as in Method 2 above.
3. Place in a 37° C., humidified, $CO_2$ incubator until beads are confluent. Check with an inverted microscope.
4. Passage cells by mixing old beads with new beads at a ratio of 1:5.
5. Place 3 new growth chambers into a 60 mm support plate. Each growth chamber should contain 200 ul of the old and new bead mixture and the plate should contain 5.0 ml of medium.
6. Return to the incubator, passage when confluent.

PRODUCTION OF HUMAN MONOCLONAL ANTIBODY

Growth chambers having a molecular weight cutoff of approximately 1,000,000 daltons are used for the production and isolation of relatively large molecular weight substances secreted by a cell culture.

For applications where large scale procedures are not required, the growth chamber methodology of the present invention permits direct harvesting of secretory products, including immunoglobulins. Production of monoclonal antibodies from cells grown in the growth chamber is approximately 5 to 10 fold greater than production by an equivalent number of cells grown in plastic flasks. No special equipment is required other than standard tissue culture items.

CHARACTERISTICS OF ULTRACLONE GROWTH CHAMBERS

Because of the highly permeable nature of the growth chambers, cells growing inside the chambers have complete access to the growth medium in the support plate. Similarly, metabolic waste products diffuse out of the chambers and are rapidly diluted. Because of these unique properties, cells are able to grow to much higher densities within the chambers compared to conventional plastic. Growth chambers with a molecular weight cutoff of approximately 1,000,000 daltons are used to collect secreted metabolic products, including immunoglobulins, from the interior compartment of the growth chamber. The permeability of the chamber wall for human IgM is approximately 2% per 24 hours. Thus, using 24 hour collection periods, approximately 98% of the available secreted IgM is recovered from the interior compartment of the growth chamber.

PRODUCTION OF HUMAN MONOCLONAL IgM FROM BL-2 CELLS

BL-2 cells are a transformed human B-lymphocyte cell line. These cells are routinely cultured in RPMI-1640 supplemented with 10% fetal bovine serum, L-glutamine, sodium pyruvate, nonessential amino acids, and gentamicin. When grown under standard tissue culture conditions in 75 $cm^2$ flasks, BL-2 cells secrete approximately 2.5 ug IgM/$10^6$ cells/24 hours. Under these conditions the maximum concentrations of IgM which can be achieved in a 24 hour period is 10 ug/ml (10 ml/flask, $4 \times 10^6$ cells/ml). At these levels, production can only be maintained for a few days before the culture begins to deteriorate.

Using growth chambers of this invention, both IgM production and culture longevity are significantly improved. $4 \times 10^6$ BL-2 cells in 1.0 ml were seeded into the interior compartment of a single growth chamber, and 6.0 ml of growth medium were added to the support plate. Cultures were refed daily by replacing all of the medium inside the growth chamber (1.0 ml) and half of the medium in the support plate (3.0 ml). At selected intervals, supernatants were removed from both interior and exterior compartments and tested for IgM levels. The results of this experiment showed that initial levels of IgM production for the first week were 10 ug/ml/24 hours inside the growth chamber and 0.05 ug/ml/24 hours outside the growth chamber. Thereafter, production stabilized at 40 ug/ml/24 hours inside the growth chamber and 0.15 ug/ml/24 hours outside the growth chamber. By refeeding cultures daily, this production level is maintained for several months. Thus, from a single growth chamber and an initial starting inoculum of only $4 \times 10^6$ cells, it was possible to collect greater than 1 mg IgM per month at a concentration of approximately 40 ug/ml.

The maximum concentration of IgM which could be achieved by not harvesting supernatants for 72 hours was 80 ug/ml inside the chamber and 1.2 ug/ml outside the chamber.

IV. OTHER EMBODIMENTS (a) Because of the molecular weight cutoff imposed by the gel structure of the growth chambers, it also is possible to seed IgM-producing cells into growth chamber in a serum-free medium while maintaining standard serum concentrations in the outer compartment. Under these conditions the cells still have access to all serum components of less than 1,000,000 daltons. The IgM in supernatants collected from inside the growth chamber is then easily separated from the other low molecular weight components of the medium by standard gel filtration chromatography.

(b) Because the gel structure of the growth chamber allows cells in the chambers continuous access to a large pool of nutrient medium, it is possible to seed lymphocyte cells into the growth chambers, allow such cells to reach maximum density and then maintain that cell density in long-term culture by periodically changing only the nutrient growth medium surrounding the growth chamber without diluting, removing or subculturing the cells. Under these conditions the cells remain viable and continue to produce secretory products, such as immunoglobulins, in levels comparable to those described above.

Further modifications and changes in the growth chambers and methods of culture of both anchorage-independent and anchorage-dependent cells will become apparent to those skilled in such arts from the foregoing disclosures. All such modifications and changes coming within the spirit and scope of the following claims are intended to be covered thereby:

I claim:

1. A cell growth chamber for anchorage independent cell growth therein, said growth chamber having a generally continuous cylindrical vertical wall of substantially uniform thickness with the foot of the interior wall surface terminating around its circumference with the outer circumference of an integral convex bottom wall to form a single cylindrical fluid container within said chamber having a single annular volume adjacent said foot of said interior cylindrical wall at a level substantially lower than the central portion of said bottom wall for concentrating the growth of anchorage-index cells in said annular volume, said chamber and bottom walls being formed of a gel matrix having a surface disallowing attachment of anchorage-dependent cells over the full interior of said chamber, and said gel matrix being capable of retaining said uniform thickness of said chamber walls while immersed in a cell-growth medium, and having a permeability sufficient to permit passage of cell-growth nutrient and waste product solutes through said cylindrical vertical wall while so immersed.

2. A cell-growth chamber in accordance with claim 1 wherein said gel matrix contains from 85% to 99.5% water.

3. A cell-growth chamber in accordance with claim 2 wherein said gel matrix is from 1% to 5% polyacrylamide and from 99% to 95% water.

4. A cell-growth chamber in accordance with claim 2 wherein said gel matrix is from 0.5% to 15% agar and from 99.5% to 85% water.

5. A cell-growth chamber in accordance with claim 1 wherein said gel matrix is a cross-linked acrylamide and sufficient water adequate to prevent cell attachment on the surface of said gel.

* * * * *